United States Patent [19]

Berman et al.

[11] Patent Number: 5,197,983
[45] Date of Patent: Mar. 30, 1993

[54] LIGAMENT AND TENDON PROSTHESIS

[75] Inventors: Andrew B. Berman; William C. Bruchman; Stanislaw L. Zukowski, all of Flagstaff, Ariz.

[73] Assignee: W. L. Gore & Associates, Inc., Newark, Del.

[21] Appl. No.: 747,595

[22] Filed: Aug. 20, 1991

Related U.S. Application Data

[63] Continuation-in-part of Ser. No. 184,470, Apr. 19, 1988, abandoned.

[51] Int. Cl.$^5$ .............................................. A61F 2/08
[52] U.S. Cl. .................................................... 623/13
[58] Field of Search ........................ 623/11, 12, 13, 66

[56] References Cited

U.S. PATENT DOCUMENTS

| | | |
|---|---|---|
| 3,176,316 | 4/1965 | Bodell . |
| 3,513,484 | 5/1970 | Hausner . |
| 3,545,008 | 12/1970 | Bader . |
| 3,613,120 | 10/1971 | McFarland, Jr. ......... 128/DIG. 21 |
| 3,797,047 | 3/1974 | Pillet ............... 128/DIG. 21 |
| 3,805,300 | 4/1974 | Tascon-Alonso et al. ...... 128/DIG. 21 |
| 3,896,500 | 7/1975 | Rambert . |
| 3,953,896 | 5/1976 | Treace . |
| 3,971,670 | 7/1976 | Homsy . |
| 3,973,277 | 8/1976 | Semple . |
| 4,034,763 | 7/1977 | Frazier . |
| 4,127,902 | 12/1978 | Homsy ................. 623/1 |
| 4,129,470 | 12/1978 | Homsy . |
| 4,149,277 | 4/1979 | Bokros . |
| 4,208,745 | 6/1980 | Okita . |
| 4,209,859 | 7/1980 | Hoffman . |
| 4,246,660 | 1/1981 | Wevers . |
| 4,248,924 | 2/1981 | Okita . |
| 4,255,820 | 3/1981 | Rothermal . |
| 4,301,551 | 11/1981 | Dore . |
| 4,345,339 | 8/1982 | Muller . |
| 4,400,833 | 8/1983 | Kurland . |
| 4,455,690 | 6/1984 | Homsy . |
| 4,469,101 | 9/1984 | Coleman . |
| 4,483,023 | 11/1984 | Hoffman, Jr. . |
| 4,550,730 | 11/1985 | Shalaby et al. . |
| 4,576,608 | 3/1986 | Homsy ................. 623/11 |
| 4,584,722 | 4/1986 | Levy et al. . |
| 4,610,688 | 9/1986 | Silvestrini . |
| 4,662,886 | 5/1987 | Moorse et al. ......... 623/13 |
| 4,668,233 | 5/1987 | Seedhom . |
| 4,731,084 | 3/1988 | Dunn et al. . |
| 4,755,183 | 7/1988 | Kenna . |
| 4,773,910 | 9/1988 | Chen et al. . |
| 4,790,850 | 12/1988 | Dunn et al. . |
| 4,795,466 | 1/1989 | Stuhmer et al. . |

FOREIGN PATENT DOCUMENTS

| | | |
|---|---|---|
| 106501A | 9/1982 | European Pat. Off. ......... 623/13 |
| 145492 | 6/1985 | European Pat. Off. . |
| 169045 | 1/1986 | European Pat. Off. . |
| US84/00770 | 12/1984 | PCT Int'l Appl. . |
| 1602834 | 11/1981 | United Kingdom . |

OTHER PUBLICATIONS

Clinical Orthopaedics vol. 186:202 (1985) Gore--Tex TM expanded PTFE prosthetic ligament; Bolton, et al.

Journal of Bone and Joint Surgery; vol. 58A No. 8 (1976) Cruciate Ligament Prosthesis Properties; Grood, et al.

*Primary Examiner*—David Isabella
*Assistant Examiner*—Gina M. Gualtieri
*Attorney, Agent, or Firm*—Dena Meyer Weker

[57] ABSTRACT

This invention provides for an improved implantable prosthetic device and in particular to a prosthetic ligament or tendon. One process provides for a means by which tensile loads may be transferred from one-load bearing member of the prosthesis to another so that damage at different sites is isolated. Another process provides a means by which the prosthesis is more abrasion resistant.

6 Claims, 16 Drawing Sheets

Fig. 4
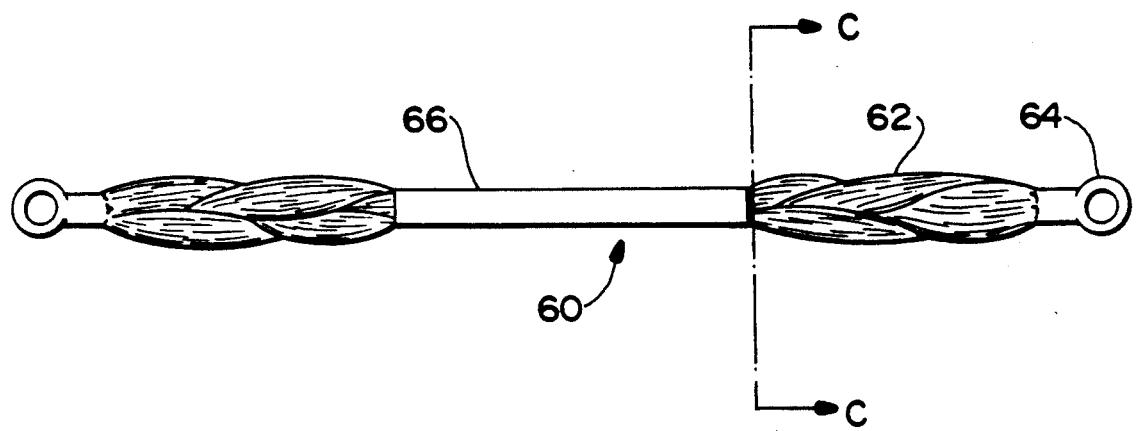
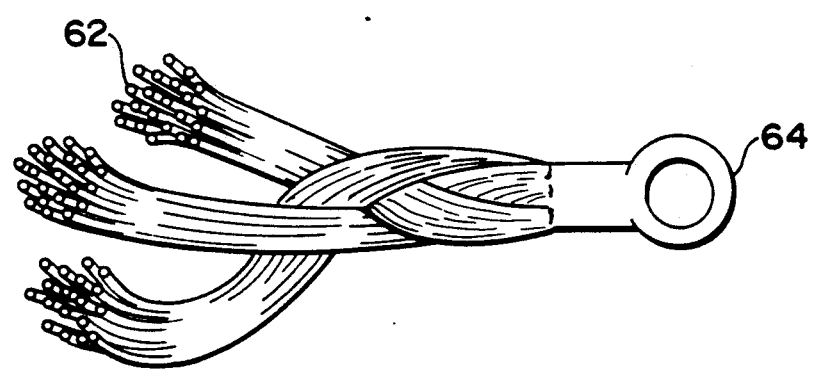
Fig. 4b

Fig. 7
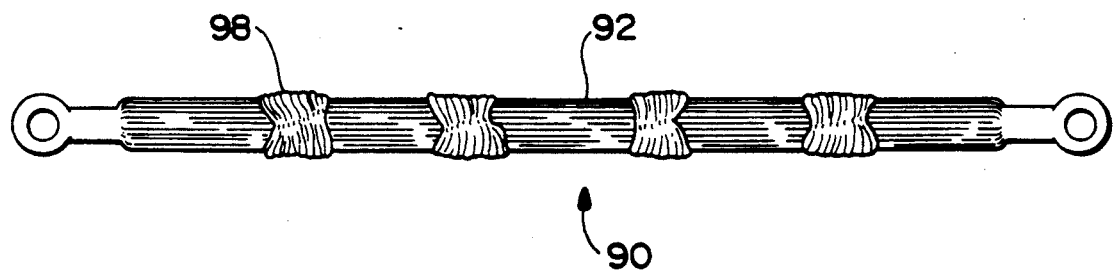
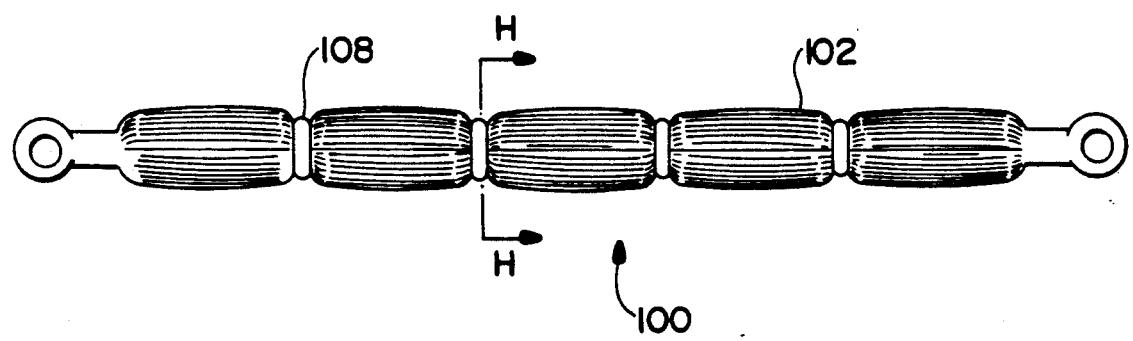
Fig. 8

LIGAMENT AND TENDON PROSTHESIS

RELATED APPLICATION

This application is a continuation-in-part application of Ser. No. 07/184,470 filed on Apr. 19, 1988 now abandoned

FIELD OF THE INVENTION

The present invention relates in general to an improved implantable prosthetic device and in particular to a prosthetic ligament or tendon.

BACKGROUND OF THE INVENTION

Ligaments are load-bearing structures that connect two skeletal members. Tendons are load-bearing structures that attach muscle to bone. Occasionally, the natural ligament and tendon will fail or need repair. The generally accepted method of reconstruction of ligaments and tendons is through the use of tissue transplanted to the defect site from elsewhere in the body. Reconstructions often fail due to a number of factors, including insufficient strength of the transplanted tissues, dependence of the transplanted tissue on revascularization for viability and inadequate strength of attachment or fixation of the transplanted tissue.

There have also been many attempts to develop a prosthetic replacement for damaged ligaments and tendons. Many of these attempts have often either failed or have brought on a new set of complications.

It is generally recognized that one of the necessary properties for a successful ligament or tendon prosthesis is ultimate fixation by host tissue. This is desirable because fixation by screws, staples, or other rigid devices is unlikely to persist without deterioration of fixation strength over time. Many attempts have been made to provide for tissue ingrowth into a prosthetic ligament device. Included among these attempts are:

(1) U.S. Pat. Nos. 3,971,670; 4,127,902; and 4,129,470 to Homsy; U.S. Pat. No. 4,149,277 to Bokros and 4,668,233 to Seedhom et al, all of which teach attachment through tissue ingrowth into porous areas of the prosthetic devices;

2) U.S. Pat. No. 3,613,120 to MacFarland; U.S. Pat. No. 3,545,008 to Bader; and U.S. Pat. Nos. 4,209,859 and 4,483,023 to Hoffman; all of which teach tissue attachment to porous fabrics with various methods of maintaining apposition to the repaired tissue.

An expanded polytetrafluoroethylene prosthetic ligament, described in U.S. Pat. No. 5,049,155 teaches the use of expanded polytetrafluoroethylene (hereinafter PTFE) in a single continuous filament looped to form parallel strands in which the strands are fixed together at the ends to form at least one eyelet. This product has proved to be a significant improvement over the above devices. In some circumstances, however, there has been evidence of non-uniform tensile loading across the cross-section of the prosthesis arising from non-uniform fixation by tissue and of stress concentrations and abrasion in areas where there is contact with bone edges.

In prosthetic devices that allow for tissue ingrowth, the ingrowth by host tissues may be a non-uniform occurrence whereby sections of the prosthetic device may become well fixed by tissue attachment while others may not become fixed at all. Non-uniformity is especially apparent during the period when tissue begins to grow into the device. The net effect of this variable tissue fixation is a great variation in the effective length of load-bearing members. As tissue grows into some portions of the prosthesis, the effective lengths of those portions are shortened to the distance between where the ingrowth has occurred. This is illustrated in FIG. 1a wherein the length of non-ingrown load-bearing members is the distance between the two fixation sites as designated by $L_0$ and the shortened length of ingrown load-bearing members is designated by $L_1$. When the prosthesis is subjected to tensile loading, those shorter load-bearing members which are fixed by tissue undergo a greater strain than those members which have no ingrowth. Consequently, the shorter members are subject to rupture first. Upon the rupture of these members, the loads are transferred to the next shortest members, and so on, causing a progressive rupture of the cross-section of the prosthesis at a relatively low load.

Another failure mode of prosthetic ligaments or tendons is a result of the methods of attachment to bony skeletal members. Many of these methods involve drilling tunnels in the connecting bones, routing the prosthesis through the tunnels, and fixing the ends to the bones. In vivo, prosthetic devices are subject to tension and flexion at multiple sites along the longitudinal axis of the device causing high stress concentrations at these sites. These stress concentrations, combined with relative movement of the prosthesis, may result in early failures due to abrasion and multi-site rupture of individual load-bearing members. Two major sites of impingement of a cruciate ligament prosthesis in the knee, for example, are the intra-articular bone tunnel exits on the tibia and femur, with various other sites in the intercondylar notch of the femur as well.

The severity of multiple site damage to a multistranded prosthesis is due to the accumulation of damage. This is illustrated in FIG. 1b wherein a hypothetical prosthesis has a total of 6 load-bearing members. In FIG. 1b, three strands are cut at one site and three strands are cut at another site. The prosthesis has lost all of its tensile strength since there are no intact load-bearing members left. This example illustrates how even slight to moderate damage at several different sites can result in severe or total loss of strength of the prosthesis due to the cumulative effect of local damage.

SUMMARY OF THE INVENTION

The present invention provides an improved structural prosthetic device for repair or replacement of the soft tissue of the musculoskeletal system, particularly tendons and ligaments. One of the processes produces a novel prosthesis comprised of a plurality of polymeric, load-bearing members that provide ultimate fixation by tissue ingrowth. The improvement lies in providing a means by which tensile loads may be transferred from one load-bearing member to another so that damage that occurs at different sites along the prosthesis is isolated. This provides a prosthesis that is more resistant to damage whether the damage occurs as a result of abrasion or as a result of uneven loading due to non-uniform tissue ingrowth.

The invention further provides an improved prosthesis that achieves the purposes above wherein one set of embodiments comprise individual load-bearing members unified together at one or more points along the length of the prosthesis to form unification sites. These unification sites can be achieved by uniting the individual load-bearing members to one another by, for example, bonding using heat, pressure, chemicals such as adhesives, or by mechanical means or any combination of the above. Embodiments may also utilize load-bearing members that have sufficient elasticity or recovery to compensate for differential loading.

BRIEF DESCRIPTION OF THE DRAWINGS

FIG. 4 is a schematic perspective view of another prosthesis constructed in accordance with the present invention.

FIG. 4b is an enlarged view of the cross-section along line C—C of FIG. 4 of an alternative embodiment.

FIG. 7 is a schematic perspective view of another prosthesis constructed in accordance with the present invention.

FIG. 8 is a schematic perspective view of another prosthesis constructed in accordance with the present invention.

DETAILED DESCRIPTION OF THE PREFERRED EMBODIMENTS

The inventive article and process described herein is to provide an improved synthetic prosthesis for replacement or reconstruction of ligaments or tendons. The prosthesis provides for ultimate fixation by tissue ingrowth directly into tensile load-bearing members wherein the improvement reduces the loss in strength which may result from non-uniform tissue ingrowth and from multiple site impingement or abrasion. An alternative embodiment of this device is constructed from polymeric materials that exhibit high elongation to failure along with minimal non-recoverable deformation.

Among the polymeric materials useful in this invention are polyester, polyethylene, polypropylene, siloxane, polyurethane, polyimide, polyamide, polyaramide, and polytetrafluoroethylene. The preferred material for the improved prosthetic is porous PTFE such as described in U.S. Pat. Nos. 3,953,566, and 4,187,390, both of which are incorporated by reference. Porous PTFE of these patents is generally characterized as having a microstructure consisting of nodes interconnected by fine fibrils and having a void volume of greater than 30% and a high matrix tensile strength. Several variations of porous PTFE are suitable for use in this invention. One type of porous PTFE is made in accordance with U.S. Pat. No. 3,953,566 that has not undergone final heat treatment to amorphously lock porous PTFE.

Another suitable porous PTFE material is made in accordance with U.S. Pat. Nos. 4,598,011 and 4,482,516, also both of which are incorporated by reference, wherein the material has a coarse microstructure having relatively large nodes and long fibrils.

Alternatively, a suitable porous PTFE material may possess either rapid recovery or elastic characteristics. Porous PTFE having rapid recovery characteristics is disclosed in U.S. Pat. Nos. 4,877,661 and 5,026,513.

Figure 1A:
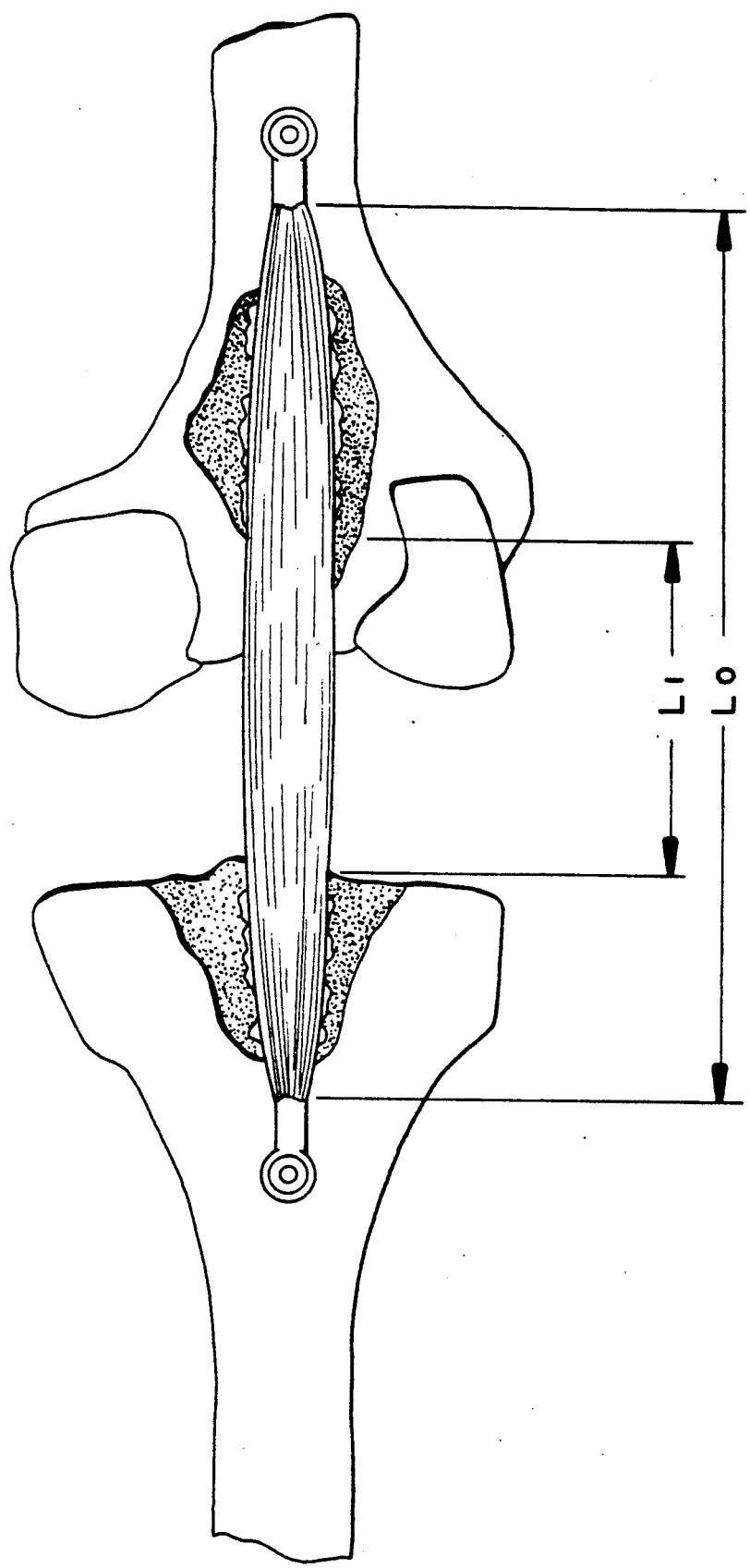
FIG. 1a shows the effective lengths of load-bearing members with no tissue fixation $L_0$ and with tissue fixation $L_1$.
Figure 1C:
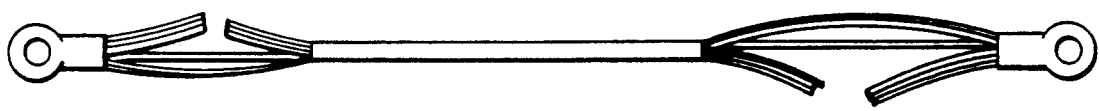
FIG. 1c shows the isolation of damage using the present invention.
Figure 1B:
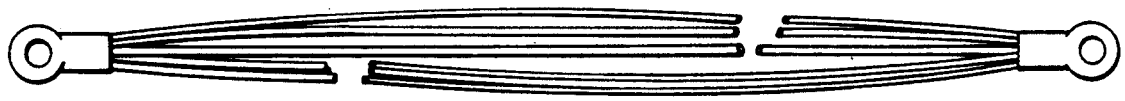
FIG. 1b shows the effect of cumulative damage.

Embodiments of the present invention provide a means for individual load-bearing members to transfer tensile forces between one another. This ability to transfer tensile loads is achieved by providing one or more unification sites wherein load-bearing members are gathered and bonded together (i.e. unified). The members must be sufficiently bonded at each of these sites to allow the transfer of tensile forces from one load-bearing member to another. Consequently, accumulation of damage at multiple sites is prevented. FIG. 1c shows the hypothetical prosthesis described above having a single unification site and two discrete compartments. Here, the same number of load-bearing members as in FIG. 1b are cut; however, due to the unification site, tensile forces are transferred and the overall loss of strength of the device is minimized. Damage at different sites is no longer cumulative.

Figure 2A:
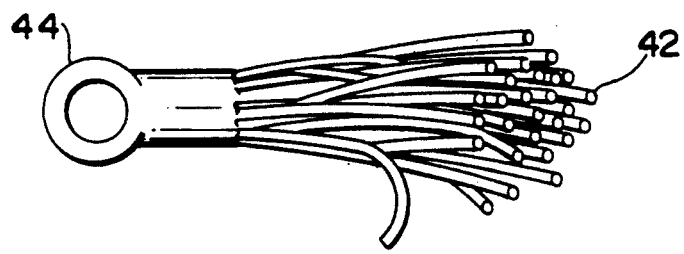
FIG. 2a is an enlarged view of the cross-section along line A—A of FIG. 2.
Figure 2:
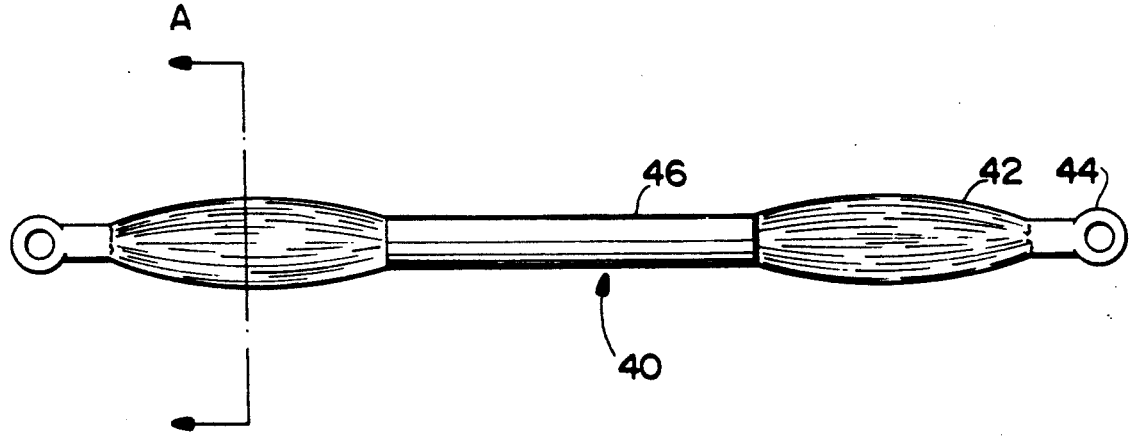
FIG. 2 is a schematic perspective view of one prosthesis constructed in accordance with the present invention.

FIG. 2 shows a schematic view of one embodiment 40 of the prosthetic device. In this embodiment, a strand of polymeric material, is looped about itself a multiplicity of times to form multiple loops of parallel strands 42. Each end of the multiple loops is gathered and formed into fixation sites preferably eyelets 44 for initial fixation of the prosthesis.

The unification site 46 is generally located in the central one-third of the prosthetic device, dividing it into discrete compartments, a cross-section of which is shown in FIG. 2a. The central one-third generally corresponds to the intra-articular portion of a joint in the case of a cruciate ligament prosthesis. The unification site not only isolates damage which may occur at the edges of the bone tunnels, but also makes this portion of the device more abrasion resistant.

The unification site 46 is made by gathering the strands 42 of the device, compressing them together under pressure and heating them so that the strands are adhered together. A film of polymeric material, preferably a film of porous PTFE, is wrapped around this compressed region, compressed further, and heated thereby binding and reinforcing all strands.

Figure 3A:
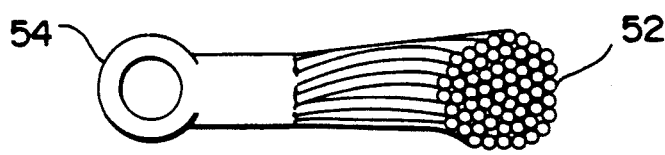
FIG. 3a is an enlarged view of the cross-section along line B—B of FIG. 4.
Figure 3:
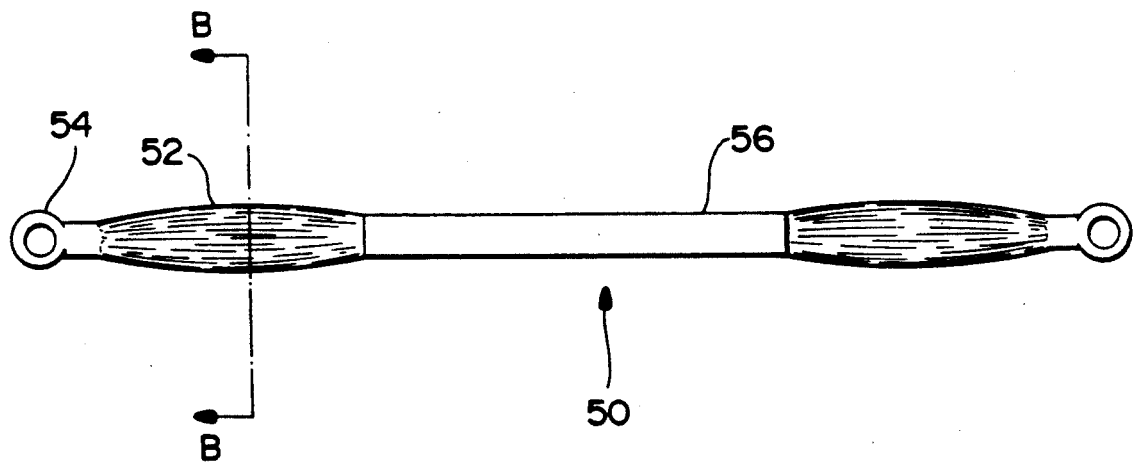
FIG. 3 is a schematic perspective view of one prosthesis constructed in accordance with the present invention.

An alternative embodiment of the device is shown in FIGS. 3 and 3a. Here, the device is comprised of individual strands 52 and is identical in construction to that shown in FIG. 2. The device is tensioned bringing all of the individual strands together and heated to above about 345° C. so that all strands are heated to above the crystalline melt point of PTFE. The strands retain their shape and integrity, but are sufficiently adhered to one another so that tensile forces may be transferred from one strand to another. This allows strands having shorter effective lengths to share the load with strands having longer effective lengths. An enlarged cross-sectional view showing the adhesion of the strands 52 to one another is shown in FIG. 3a in contrast to those shown in FIG. 2a wherein the strands are separate. Eyelets 54 similar to those described above are also constructed.

Optionally, to provide higher degree of abrasion resistance, the central one-third of the device 56 may be compressed, wrapped, and recompressed as previously described.

Figure 4A:
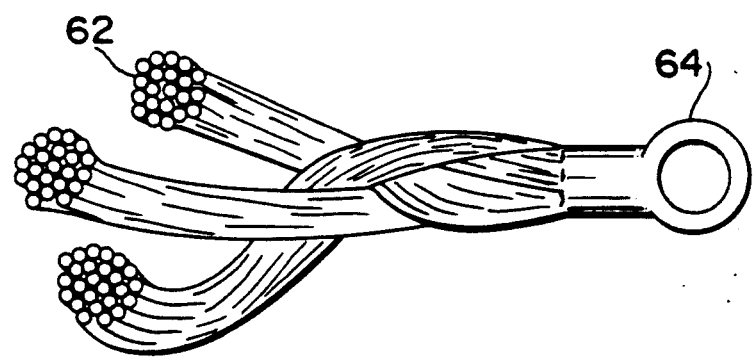
FIG. 4a is an enlarged view of the cross-section along line C—C of FIG. 4.

Another embodiment is comprised of a braid of polymeric material, preferably porous PTFE, as shown in FIG. 4. Again, the ends of the device may be formed into eyelets 64. The braided strands 62 are gathered and unified with a wrap of polymeric material 66 as previously described. The entire device may be tensioned and heated as described previously to bond the individual strands 62 together along the length of the device as shown in FIG. 4a. Alternatively, as shown in FIG. 4b, the strands need not be bonded together.

Figure 5A:
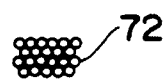
FIG. 5a is enlarged view of the cross-section along line D—D of FIG. 5.
Figure 5B:
FIG. 5b is an enlarged view of the cross-section line E—E of FIG. 5.
Figure 5:
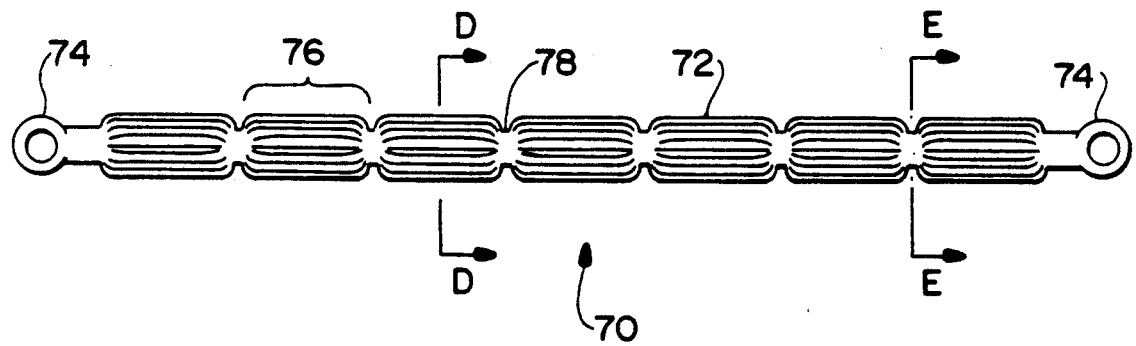
FIG. 5 is a schematic perspective view of one prosthesis constructed in accordance with the present invention.

In yet another embodiment, a device is comprised of a plurality of polymeric strands, the preferred polymer being porous PTFE, manufactured by but not limited to any of the processes described above, wherein the strands are unified at multiple selected sites such that the device is segmented into a plurality of individual compartments 76, as illustrated in FIG. 5.

The device 70 is comprised of fixation eyelets 74 and individual strands 72 that are divided into a number of compartment segments 76 by thermally bonding the strands 72 at selected unification sites 78 along the longitudinal axis of the device. The number and placement of the unification sites vary and is dependent upon the length and application of the device. The length of an individual segment 76, (i.e., a distance between two consecutive unification sites 78), may vary, but is preferably greater than 5 mm. and most preferably is between about 10 to 15 mm. FIG. 5a shows an enlarged cross-section of the segment 76 wherein the strands act as individual load-bearing members. FIG. 5b shows an enlarged cross-section of the unification sites 78 wherein the strands act as a single unified body. The load-bearing members 72 are thus able to transfer loads such that tensile forces on individual load-bearing members are distributed to all other members.

Figure 6:
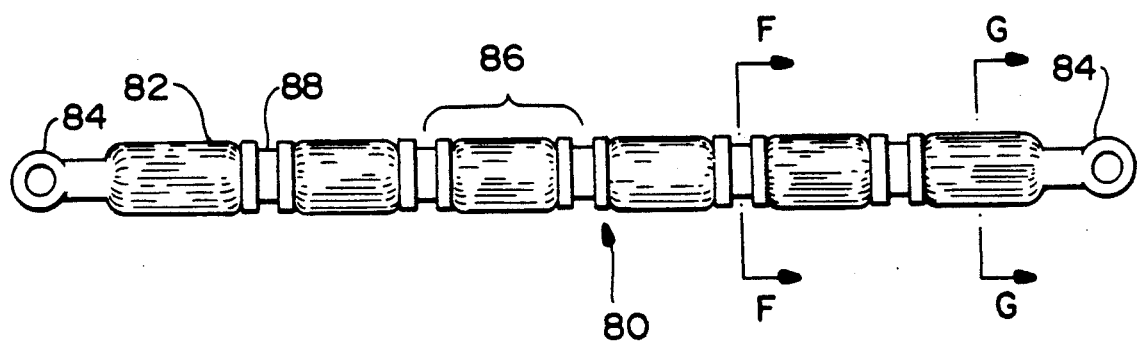
FIG. 6 is a schematic perspective view of one prosthesis constructed in accordance with the present invention.
Figure 6B:
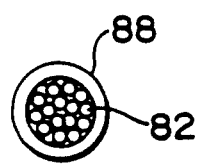
FIG. 6b is an enlarged view of the cross-section along line F—F of FIG. 6.
Figure 6A:
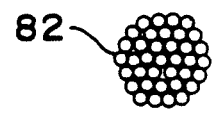
FIG. 6a is an enlarged view of the cross-section along line G—G of FIG. 6.

FIG. 6 shows an embodiment 80 comprising strands 82, fixation eyelets 84, and circumferential restraints such as plugs 88, wherein the plugs create unification sites 88 and a number of compartments 86. The strands 82 are comprised of a flexible polymer, preferably porous PTFE. Strands 82 are unified at selected intervals along the longitudinal axis of the device by plugs 88 that are thermally, chemically, or mechanically bonded to the strands. Plugs 88 are made of the same polymer as the strands 82 or any other high-strength, biocompatible material. The outer diameter of the plug 88 is chosen such that the plugs 88 fit snug into the bone tunnels. The strands within the plugs, as shown in FIG. 6b, are bonded together so that they are sufficiently adhered to each other to distribute the load among them. The plugs 88 are spaced along the device so that one or more of them are placed within each bone tunnel after implantation.

FIG. 7 shows another embodiment wherein the device 90 is segmented along its longitudinal axis at unification sites by tying the individual strands 92 into knots 98.

Figure 8A:
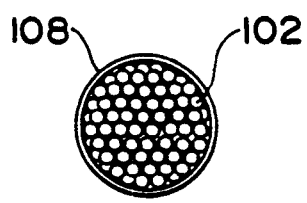
FIG. 8a is an enlarged view of the cross-section along line H—H of FIG. 8.

FIG. 8, illustrates still another embodiment of the inventive device whereby circular rings 108 are applied around load-bearing strands 102 at selected unifications along the longitudinal axis of the device 100. The rings 108 are made of stainless steel or any other high strength biocompatible material. The load-bearing members 102 are able to share a tensional load due to frictional cohesiveness created by compressive forces of the rings. FIG. 8a is an enlarged view of the cross-section H—H shown in FIG. 8. It shows compressed load-bearing strands 102 under the unifying ring 108.

EXAMPLE 1

SINGLE UNIFICATION SITE

A GORE-TEX ™ Cruciate Ligament Prosthesis commercially available from W. L. Gore & Associates, Inc. (Flagstaff, Ariz.) was used as the precursor device for this example. The ligament consisted of a tripartite braid of multiple strands of porous PTFE with eyelets for use in fixation.

First, the precursor device was unbraided. It was then placed on a rack with pins through the eyelet. Tension was applied to the device while the central one-third was compressed in a heated die having approximately a 0.250 inch diameter. It was held compressed at 330° C. for 3 minutes, causing the individual strands to adhere to each other in a compressed segment. After removal of the device from the die, the compressed segment was wrapped with 60 layers of porous PTFE film made in accordance with U.S. Pat. No. 3,593,566. The wrapped segment was then placed in another heated die and held compressed at 370° C. for 3.5 minutes. This second heat treatment and compression caused the film to adhere to itself and to the load-bearing members.

The resulting device was similar to that shown in FIG. 2 where the overall construction was comprised of strands 42 of microporous PTFE having two eyelets 44 and a unification site 46. The unification site allowed strands to transfer loads to one another, providing equal load distribution. The unification site also provided abrasion resistance.

EXAMPLE 2

STRANDS ADHERED

A prosthetic device was obtained and constructed similar to that described in example 1 in which a unification site was made in an unbraided GORE-TEX ™ Cruciate Ligament Prosthesis.

The device was placed under tension in an oven heated to 385° C. and heated for 5 minutes, causing the strands to adhere together.

The resulting device produced a ligament similar to that shown in FIG. 3. The adherence of strands allowed tensile forces to be transferred from strand to strand, equalizing load distribution.

EXAMPLE 3

MULTIPLE UNIFICATION SITES

The basic precursor of this device was identical to that described in examples 1 and 2 wherein a GORE-TEX ™ Cruciate Ligament Prosthesis was unbraided.

Figure 9:
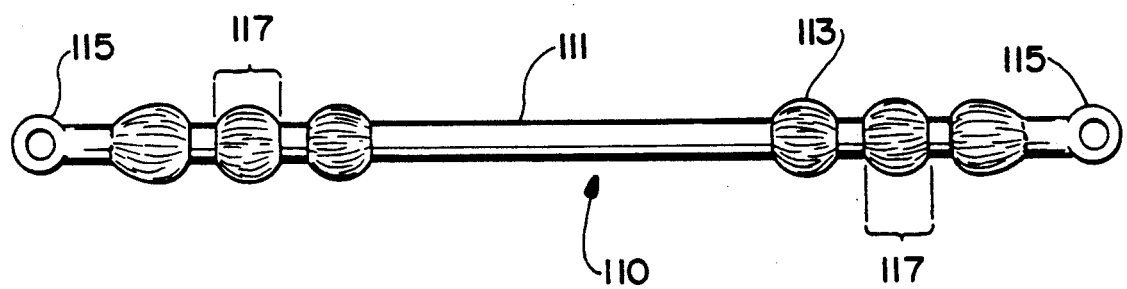
FIG. 9 is a schematic perspective view of one embodiment of the present invention.

A central unification site was made similar to that described in Examples 1 and 2 and shown in FIG. 9 wherein the central unification site 111 covers the central one-third of the device 110.

An additional cylindrical die was used to compress strands 113 at four additional sites, two sites at each end between the central unification 111 and eyelets 115. The unification sites 117 were spaced 1.5 cm apart and were about 0.25 cm in length. The device was restrained in a rack with pins through eyelets to prevent shrinkage. Each of the four additional sites 117 was compressed for two minutes at a temperature of 370° C. After this precompression, the sites were wrapped with 60 layers of a film of porous PTFE. Each site was then recompressed for four minutes in a die heated to a temperature of 370° C. The device was removed from the rack after complete cooling of these unification sites.

EXAMPLE 4

STRYKER ® DACRON ® LIGAMENT WITH UNIFICATION SITE

A Dacron ® Augmentation Graft commercially available from Stryker Corp. (Kalamazoo, Mich.) was used as the precursor device for this example. The device consisted of four high strength load-bearing tapes within a Dacron ® velour sleeve.

Figure 10:
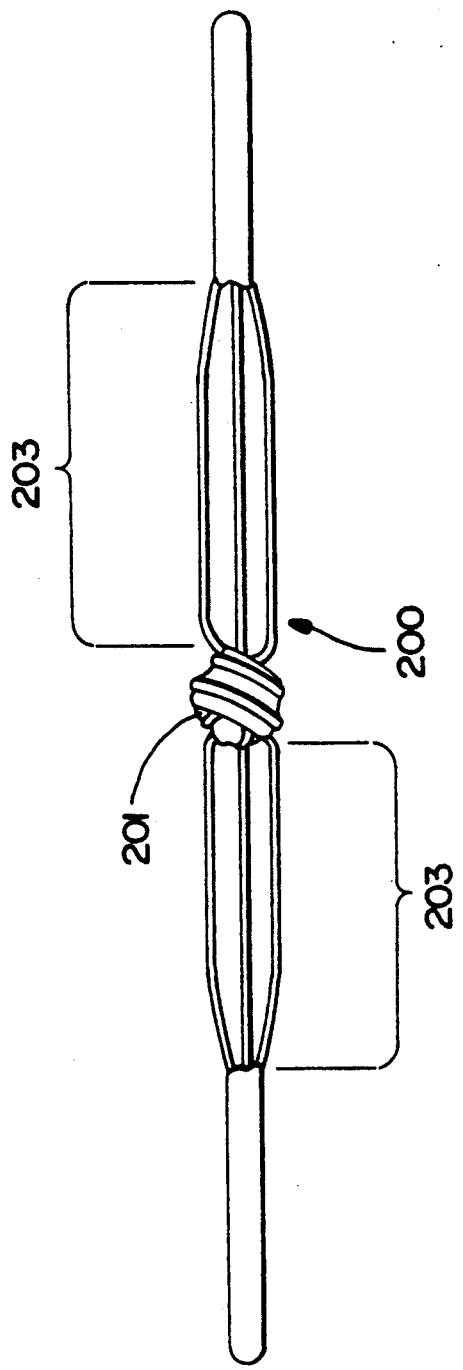
FIG. 10 is a schematic perspective view of another prosthesis constructed in accordance with the present invention.

The precursor device was modified to create two compartments 203 of load-bearing members, separated by one unification site 201, as shown in FIG. 10.

The unification site 201 was constructed by tying a knot in the device 200. After applying tension to secure the knot, the unification site was further reinforced with an adhesive, Loctite ® #495.

A comparison was made between a standard control Stryker device and one made in accordance with the present invention. To mimic abrasion, two of the four load-bearing strands were cut on each of the control and modified devices. The strands were cut at two sites, two inches apart, leaving three strands intact at each site. For the modified device, one strand was cut in each compartment.

Each device was then tested in tension to failure on an Instron #1331, tensile testing machine. The crosshead speed was 280 mm/minute which corresponds to an initial strain rate of 2.6%/second for an 18 cm initial length.

Results are summarized in the table below. The device modified in accordance with the present invention demonstrated a 66% improvement in tensile strength over a control device in the presence of multi-site damage.

TABLE 1

| Device | Pounds to Break |
| --- | --- |
| Control Device | 255 |
| Device with one Unification site | 425 |

EXAMPLE 5

A GORE-TEX ® Cruciate Ligament Prosthesis commercially available from W. L. Gore & Associates, Inc. (Flagstaff, Ariz.) was used as the precursor device for this example. The ligament consisted of a tripartite braid of multiple strands of porous PTFE with eyelets for use in fixation.

Figure 11:
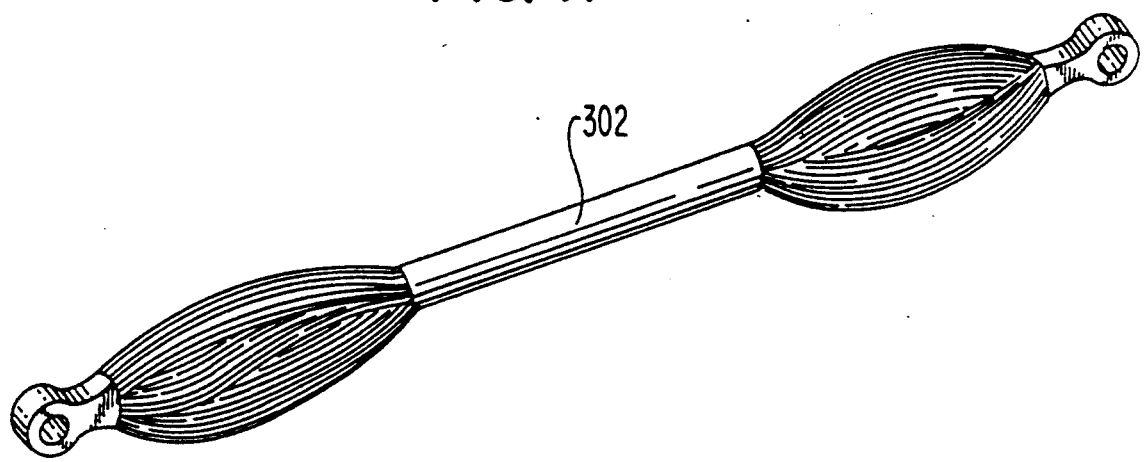
FIG. 11 is a schematic perspective of the reinforced prosthesis constructed in accordance with the present invention.
Figure 11A:
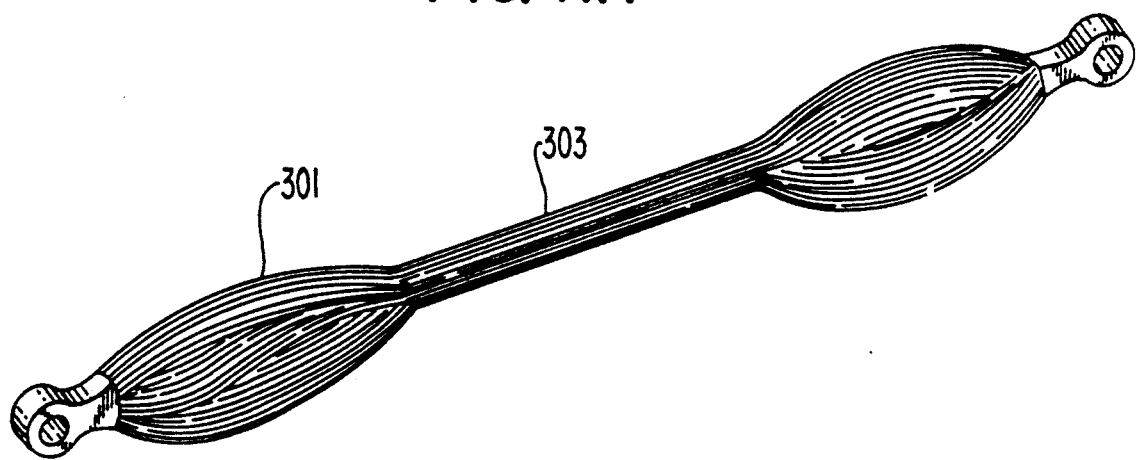
FIG. 11a is a schematic perspective of the reinforced prosthesis after the precompression step of construction.

First the precursor device was unbraided. It was placed on a rack with pins through the eyelets. Tension was applied to the prosthesis while the central region of at least 5 cm and preferably 8.5 cm was precompressed in a heated die having approximately a 0.250 inch diameter. It was held for approximately 3 minutes at a temperature of 330° C. causing the individual strands 301 to become adhered to each other in a precompressed, unified segment 303 as illustrated in FIG. 11a.

Figure 11B:
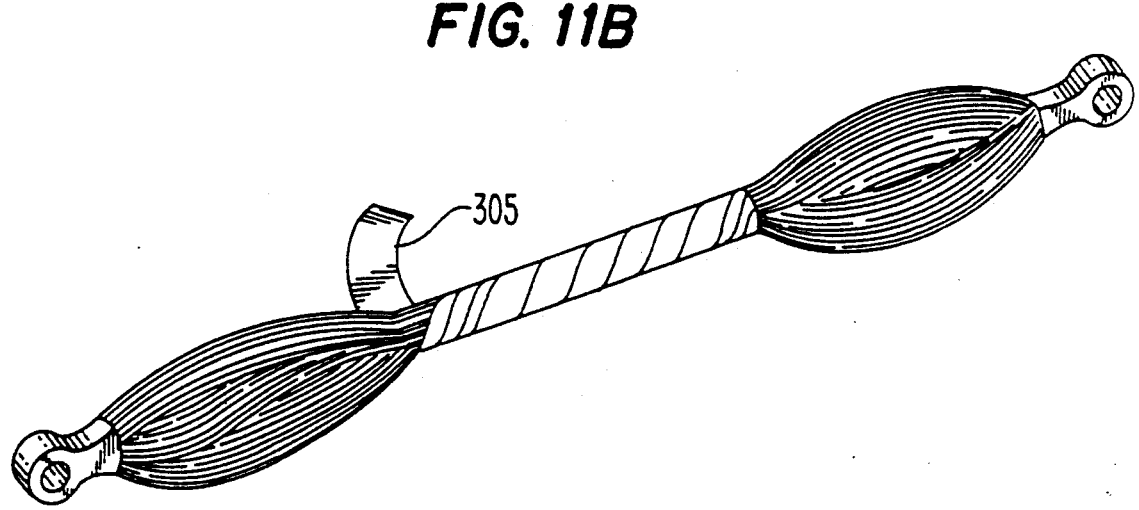
FIG. 11b is a schematic perspective of the reinforced prosthesis after the helical wrapping step of construction.

After removal of the prosthesis from the heated die, the central precompressed segment was helically wrapped as shown in FIG. 11b with 12.7 mm wide porous PTFE film 305 made in accordance with U.S. Pat. No. 3,593,566. The film was applied such that the amount of overlap in the central region was approximately 25% per wrap while the amount of overlap in the remaining one centimeter at either end of the compressed unified segment was approximately 50% per wrap. Thirty-eight passes were made resulting in approximately 55-60 layers of film in the central 6.5 cm of the compressed uniform segment and 75-80 layers in the 1 cm at either end of the compressed unified segment. Using a hot (greater than 300°.C.) probe, the loose end of the film was tacked down to prevent unwinding of the film. The purpose of the helical wrap was to provide hoop strength required to maintain the unification and provide abrasion resistance. The purpose of applying more film at the ends of the precompressed segment was to prevent flaring of the ends of the precompressed unified segment at the unified/non-unified transition.

Figure 11C:
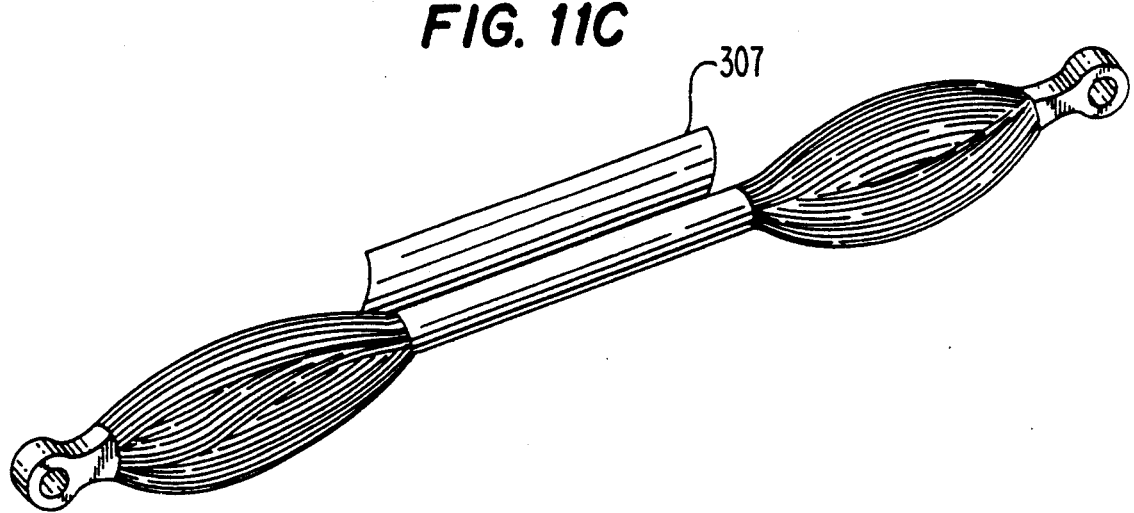
FIG. 11c is a schematic perspective of the prosthesis after the tangential wrapping step of construction.

To minimize the number of exposed film edges which could potentially catch on bone edges and consequently peel off, a second wrap component 307 was applied tangentially as shown in FIG. 11c. This second film component was made of the same PTFE film described above except that it was 5 cm and preferably 8.5 cm in width. Four layers of this film were applied by first tacking the wide film to the helically-wrapped compressed unified segment. Tacking was accomplished by placing a die heated to 375° C. on the film for 25 seconds. Four layers of film were then applied by rotating the prosthesis four times. Finally, the loose end was tacked down in a manner similar to that just described. The tangential component of the film wrap resulted in just one exposed film edge 302 running longitudinally down the length of the compressed unified helically-wrapped segment (FIG. 11).

After both the helical and tangential components of the wrap were applied, the prosthesis was placed in another heated die with a diameter of approximately 0.250 inches for approximately 3.5 minutes. This heating caused both film components to shrink, further compressing the central 8.5 cm segment of the prosthesis.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

We claim:

1. A prosthetic ligament comprising a plurality of load-bearing members of expanded porous polytetrafluoroethylene, said ligament having two fixation sites at opposite ends of the prosthetic ligament and further having at least one unification site having a length located along a longitudinal axis of the prosthetic ligament between said two fixation sites, wherein at least a portion of the length of the at least one unification site is located in a bone contacting region of the prosthetic ligament, said at least one unification site comprising gathered members helically-wrapped with a narrow film of expanded porous polytetrafluoroethylene and an outermost wrap of a wide film of expanded porous polytetrafluoroethylene surrounding said helically-wrapped, gathered members.

2. A prosthetic ligament as described in Claim 1 in which one of said at least one unification sites is a centrally located unification site between the two fixation sites and extends along said longitudinal axis of the prosthetic ligament.

3. A prosthetic ligament as described in Claim 2 in which said centrally located unification site extends for at least 5 cm along a longitudinal axis.

4. A prosthetic ligament as described in Claim 1 in which said helical wrap has a pitch that is biased to provide a greater number of layers at the ends of said wrap than in the center.

5. A prosthetic ligament as described in Claim 1 having at least two unification sites between said two fixation sites.

6. A method for manufacturing a ligament or tendon prosthesis comprising the step of providing a ligament or tendon having a plurality of expanded porous polytetrafluoroethylene members and two fixation sites at opposite ends thereof, gathering said members together at at least one unification site having a length located along a longitudinal axis of the prothesis between said two fixation sites, wherein at least a portion of the length of the at least one unification site is located in a bone contacting region between the opposite end of the prothesis, and wrapping the gathered members first with a narrow film of expanded porous polytetrafluoroethylene in a helical configuration and subsequently wrapping said at least one unification site with a wide film of expanded porous polytetrafluoroethylene so as to surround the helical wrapping.

* * * * *